United States Patent
Kraus

(10) Patent No.: US 10,238,739 B2
(45) Date of Patent: Mar. 26, 2019

(54) MANUFACTURE OF SURFACTANT-CONTAINING COMPOSITIONS WITH ENHANCED STABILITY

(71) Applicant: NOVARTIS AG, Basel (CH)

(72) Inventor: Gottfried Kraus, Marburg (DE)

(73) Assignee: NOVARTIS AG, Basel (CH)

(*) Notice: Subject to any disclaimer, the term of this patent is extended or adjusted under 35 U.S.C. 154(b) by 0 days.

(21) Appl. No.: 15/531,487

(22) PCT Filed: Dec. 2, 2015

(86) PCT No.: PCT/EP2015/078270
§ 371 (c)(1),
(2) Date: May 30, 2017

(87) PCT Pub. No.: WO2016/087479
PCT Pub. Date: Jun. 9, 2016

(65) Prior Publication Data
US 2017/0312357 A1 Nov. 2, 2017

(30) Foreign Application Priority Data

Dec. 2, 2014 (EP) .................... 14195981

(51) Int. Cl.
| | | |
|---|---|---|
| *A61K 39/39* | (2006.01) | |
| *A61K 39/00* | (2006.01) | |
| *A61K 39/145* | (2006.01) | |
| *C12N 7/00* | (2006.01) | |
| *B01D 71/68* | (2006.01) | |

(52) U.S. Cl.
CPC .............. *A61K 39/39* (2013.01); *A61K 39/00* (2013.01); *A61K 39/145* (2013.01); *B01D 71/68* (2013.01); *C12N 7/00* (2013.01); *A61K 2039/55566* (2013.01); *B01D 2325/022* (2013.01); *B01D 2325/36* (2013.01); *C12N 2760/16034* (2013.01)

(58) Field of Classification Search
None
See application file for complete search history.

(56) References Cited

U.S. PATENT DOCUMENTS

| | | |
|---|---|---|
| 5,217,648 A | 6/1993 | Beissinger et al. |
| 8,092,813 B1 | 1/2012 | Novicki |

FOREIGN PATENT DOCUMENTS

| | | |
|---|---|---|
| CN | 101 649 138 | 2/2010 |
| WO | 2011/067673 | 6/2011 |

OTHER PUBLICATIONS

Agarkhed et al., AAPS PharmSciTech, Mar. 2013, 14(1):1-9.*
Maggio, J. Excipients and Food Chem,, 2012, 3(2):45-53.*
International Search Report and Written Opinion of the International Searching Authority dated Feb. 8, 2016, which issued during prosecution of International Application No. PCT/EP2015/078270.
Database WPI, "Preparation of neutral ink by homogenizing and emulsifying ethylene glycol, polyethylene glycol, Tween 80, sodium hexametaphosphate, sodium benzoate, benzotriazole, graphite emulsion, polyacrylamide solution and emulsified silicone oil" Thomson Scientific; London, GB; Week 201021; XP002739847.

* cited by examiner

*Primary Examiner* — Nicole Kinsey White
(74) *Attorney, Agent, or Firm* — Duane Morris LLP; Thomas J. Kowalski; Mark W. Russell

(57) ABSTRACT

Improved methods for the manufacture of pharmaceutical compositions comprising at least one surfactant, involving prefiltration of the surfactant prior to formulation into final products.

14 Claims, 1 Drawing Sheet

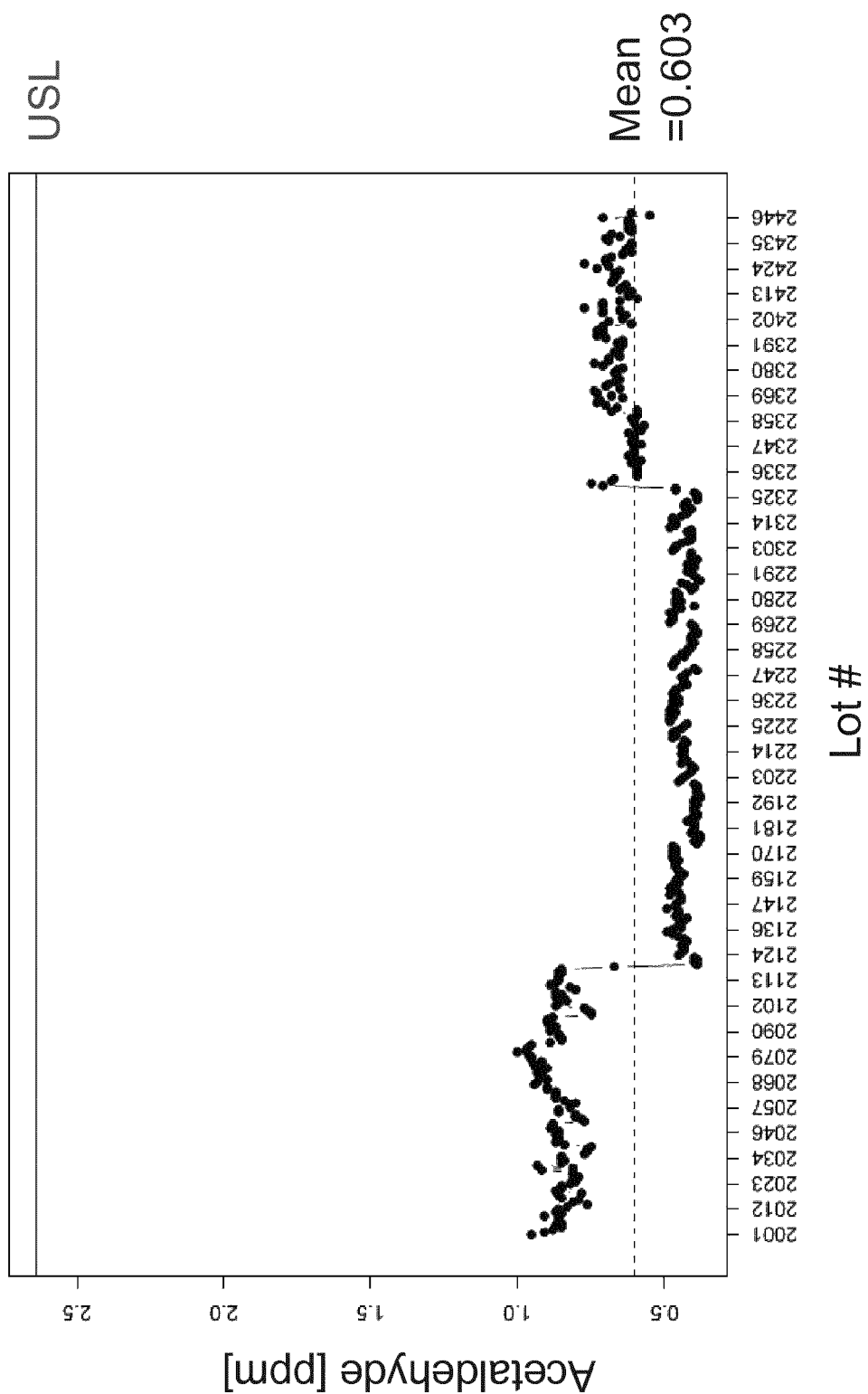

MANUFACTURE OF SURFACTANT-CONTAINING COMPOSITIONS WITH ENHANCED STABILITY

RELATED APPLICATIONS AND INCORPORATION BY REFERENCE

The present patent application is filed pursuant to 35 U.S.C. § 371 as a U.S. National Phase Application of International Patent Application No. PCT/EP2015/078270 filed on Dec. 2, 2015, claiming the benefit of priority to European Patent Application No. 14195981.7 filed on Dec. 2, 2014. The International Application was published as WO 2016/087479 on Jun. 9, 2016. The contents of each of the aforementioned patent applications are herein incorporated by reference in their entirety.

FIELD OF THE INVENTION

This invention is in the field of manufacturing compositions that include a surfactant, such as pharmaceutical compositions, and, in particular, achieving the reduction of impurities in such compositions.

BACKGROUND

Certain components of pharmaceutical, nutraceutical and cosmetic compositions are known to undergo unwanted degradation and/or chemical alterations, affecting the quality or shelf-life of such products. For instance, surfactants can degrade to generate unwanted components, e.g., polysorbates can yield unwanted carbonyl degradation products.

Surfactants are used in emulsions. The vaccine adjuvant known as "MF59" [References 1-3] is a submicron oil-in-water emulsion of squalene, polysorbate 80 (also known as TWEEN® 80), and sorbitan trioleate (also known as SPAN®85). It may also include citrate ions, e.g., 10 mM sodium citrate buffer. The composition of the emulsion by volume can be about 5% squalene, about 0.5% TWEEN® 80 and about 0.5% SPAN®85. The adjuvant and its production are described in more detail in Chapter 10 of Reference 4, chapter 12 of Reference 5 and chapter 19 of Reference 6. Polysorbate 80 and squalene are also present in the emulsion adjuvant known as "AS03" [Reference 16].

Polysorbates can undergo autooxidation, generating peroxides, aldehydes, ketones and acids. Other components in a composition, such as proteins, can be affected by some of these degradation products. For instance, conformation of proteins can change, which can affect their efficacy [References 7, 8].

In addition, squalene has been shown to undergo oxidative degradation resulting in the generation of carbonyl by-products. Photo-oxidative cleavage of squalene has been shown to produce formaldehyde, malonaldehyde, acetaldehyde and acetone [References 9], although degradation can be reduced by storage in an air-tight container, storage under nitrogen, protection from light, etc.

SUMMARY OF THE INVENTION

The present invention provides methods for improving the quality and/or shelf life of compositions that contain at least one surfactant, such as a non-ionic surfactant. The invention encompasses the recognition that certain pre-processing of a surfactant component for the manufacture of a product into which the surfactant becomes incorporated can significantly improve the quality of the resulting product. It has been found that such pre-processing can in some cases enhance the stability of the product, prolong its shelf life, and/or maintain its overall quality. Such effects may be achieved by, for example, prefiltering the surfactant component (e.g., liquid surfactants, solutions containing a surfactant, etc.) prior to formulating into a product. The invention thus offers a novel solution for improving the manufacturing process and/or the quality of surfactant-containing products by controlling the quality of an ingredient (e.g., starting material and/or intermediate) comprising a surfactant.

A number of products, in particular, pharmaceutical formulations (see below), food and nutraceutical formulations (dietary supplements, food ingredients, etc.), as well as cosmetic formulations (e.g., lotions, creams, gels, foams, etc.), are formulated with at least one surfactant. The present invention therefore may be useful for improving such products.

Pre-processing (such as prefiltration) of a surfactant component is aimed at enhancing the quality of or increasing purity of the component used as a starting material or an intermediate ingredient, by removing impurities and/or aggregates that may be present in the raw or unprocessed surfactant. Furthermore, removal of any aggregates is also beneficial if the surfactant will later be used in an apparatus which can become clogged, such as in a microfluidisation chamber.

BRIEF DESCRIPTION OF THE DRAWING

FIG. 1 depicts the acetaldehyde content measured in ppm in a number of batches of an exemplary surfactant-containing composition. Data points in the middle section of the diagram correspond to the batches that included a surfactant which had been pre-filtered, while data points in the flanking sections correspond to the batches that included a surfactant which had not been pre-filtered. All other production parameters remained unchanged.

DETAILED DESCRIPTION OF CERTAIN EMBODIMENTS

The present invention provides methods for improving the manufacturing process and/or the quality of a surfactant-containing composition. The invention described herein is therefore suitable for any products that comprise at least one surfactant, including, for example, pharmaceutical compositions, nutraceutical compositions and cosmetic compositions. The present invention offers a novel solution to improve the manufacture process and/or the quality of such compositions by improving the quality of a surfactant component itself by pretreating the surfactant as described herein. The improved methods are particularly suitable when the enhanced stability of the product is desirable.

Thus, the compositions and methods described herein are particularly useful for the manufacture of emulsion-based products. Surfactants are widely used as emulsifiers for scientific and commercial purposes. An emulsifier may be added to facilitate formation and stability of an emulsion, such as oil-in-water emulsions and water-in-oil emulsions. Emulsion-based products may be prone to destabilization by virtue of having two or more liquid components that are naturally immiscible dispersed therein, which may be thermodynamically unfavorable. For certain emulsion-based products that require a high degree of uniformity, purity, and/or stability, it is especially beneficial to ensure that the product does not undergo unwanted degradation or alteration of chemical compositions over time. Accordingly, some embodiments of the invention are drawn to improved methods for the production of oil in water emulsions, in particular methods which lead to a reduction in undesirable carbonyl impurities in the final emulsions.

Surprisingly, the inventor has found that levels of carbonyl impurities in oil-in-water emulsions can be reduced by size filtration of a surfactant (e.g., polysorbate 80), and then using this filtered material to prepare the emulsion. Without wishing to be bound by theory, the inventor believes that carbonyl degradation products in a surfactant material reside preferentially within large aggregates, and that the filtration removes such aggregates. The filtration can be achieved with a filter having a pore size larger than used in filter sterilization, and it is advantageously performed on non-aqueous surfactant (such as non-aqueous polysorbate 80) before being dissolved in water, although it is also possible to carry out prefiltration of an intermediate material that comprises the surfactant and at least part of an aqueous component. Reducing the levels of carbonyl impurities is particularly important in emulsions which contain other components which can also provide carbonyl degradation products, e.g., squalene. Thus the invention is particularly useful for manufacturing emulsion vaccine adjuvants such as "MF59" or "AS03."

Thus the invention provides bulk preparations of a pre-processed surfactant containing (i) a carbonyl level that is lower than that of the surfactant not subjected to prefiltration; and/or (ii) fewer aggregates than the surfactant not subjected to prefiltration. The phrase "bulk preparation" refers to a commercial-scale preparation of such surfactants. Typically, such a preparation has a volume of at least 50 liters, e.g., at least 75 liters, at least 100 liters, at least 125 liters, at least 150 liters, at least 175 liters, at least 200 liters, at least 250 liters, or at least 300 liters. Such pre-processed surfactants can then be used in the manufacture of any suitable products.

The invention also provides a process for preparing a surfactant comprising a step of filtering non-aqueous surfactant through a filter having a pore size between 5-50 µm. The filtered surfactant can then be used for downstream purposes, such as those disclosed herein. The process is particularly useful for preparing bulk preparations of surfactant. The process is particularly suitable for filtering non-aqueous polysorbate 80.

In another aspect, the invention provides processes for preparing a surfactant-containing formulation using a pre-processed surfactant (e.g., prefiltered surfactant). "Pre-processed" surfactants may be provided by a prefiltration step as described herein. For example, prefiltration of a surfactant in accordance with the present invention may be carried out with the use of a filter having a pore size between 5-50 µm. The prefiltered surfactant may contain a carbonyl level that is lower than that of the surfactant not subjected to prefiltration. The prefiltered surfactant may also contain fewer aggregates than the surfactant not subjected to prefiltration.

In some embodiments, the invention provides a process for preparing an emulsion (such as an oil-in-water emulsion) using a surfactant that has been pre-processed as described herein, e.g., to achieve reduced levels of carbonyl impurities and/or fewer aggregates.

In exemplary embodiments, such process may involve the following steps: (a) providing a surfactant, such as polysorbate 80, which has been prefiltered through a filter having a pore size between 5-50 µm, to provide purified (e.g., prefiltered) surfactant (e.g., polysorbate 80); and (b) combining the purified surfactant (e.g., polysorbate 80) with an oil component to provide an emulsion. In addition to the purified surfactant and the oil component, the emulsion will include an aqueous component (and, as described in more detail below, possibly further components as well). Aqueous material may be added as a third component in step (b), or may be combined with the surfactant and/or the oil prior to step (b), or may even be present in the surfactant filtered in step (a). Thus the surfactant (e.g., polysorbate 80) which is obtained in step (a) can be an aqueous solution of the surfactant (e.g., polysorbate 80), but may also be non-aqueous surfactant i.e., surfactant which has not been diluted with water (or any other aqueous material) prior to being filtered. Thus the surfactant (e.g., polysorbate 80) may be filtered in the "raw" or "bulk" condition in which it arrives from a manufacturer. Typically, step (a) of the process comprises a step of filtering the surfactant.

Similarly, the invention includes a process for preparing an oil-in-water emulsion comprising a step of combining a polysorbate 80 with an oil component, wherein the polysorbate 80 has previously been filtered through a filter having a pore size between 5-50 µm. The polysorbate 80 may have been treated between being filtered and being combined with the oil component, e.g., it may have been diluted to provide an aqueous surfactant. It is understood that the prefiltration step and the subsequent formulation step(s) may be carried out at the same site or in separate sites, and by the same person or by different people.

The invention also provides a process for preparing an oil-in-water emulsion comprising steps of: (a) filtering non-aqueous polysorbate 80, to provide purified polysorbate 80; and (b) combining the purified polysorbate 80 with an oil component to provide the oil in water emulsion. The filter used in step (a) can have a pore size between 5-50 µm, which is much larger than used for filter sterilization (e.g., 0.22 µm). Between steps (a) and (b) the purified polysorbate 80 can be combined with aqueous material (e.g., water or buffer) to give aqueous purified polysorbate 80 which is then combined with an oil component in step (b).

Similarly, the invention provides a process for preparing an oil-in-water emulsion comprising a step of combining a polysorbate 80 with an oil component, wherein the polysorbate 80 has previously been filtered in non-aqueous form.

In some embodiments, the invention provides a process for preparing an oil-in-water emulsion comprising steps of: (a) filtering non-aqueous polysorbate 80 through a filter having a pore size between 5-50 µm, to provide purified polysorbate 80; and (b) combining the purified polysorbate 80 with an oil component to provide the oil in water emulsion.

Similarly, the invention provides a process for preparing an oil-in-water emulsion comprising a step of combining a polysorbate 80 with an oil component, wherein the polysorbate 80 has previously been filtered in non-aqueous form with a filter having a pore size between 5-50 µm.

The invention also provides a process for preparing an oil-in-water emulsion comprising steps of: (a) filtering non-aqueous polysorbate 80 through a filter having a pore size between 5-50 µm, to provide purified non-aqueous polysorbate 80; (b) combining the purified non-aqueous polysorbate 80 with an aqueous material, to provide an aqueous component; and (c) combining the aqueous component with an oil component to provide the oil in water emulsion.

Similarly, the invention provides a process for preparing an oil-in-water emulsion comprising a step of combining an aqueous polysorbate 80 solution with an oil component, wherein the solution was formed by mixing an aqueous carrier with polysorbate 80 which had previously been filtered in non-aqueous form with a filter having a pore size between 5-50 μm.

The invention also provides a process for preparing a vaccine, comprising a step of combining an emulsion of the invention with an antigen. Similarly, the invention provides a process for preparing a vaccine, comprising steps of: (i) preparing an emulsion as described herein; and (ii) combining this emulsion with an antigen. In general, however, the invention has broader applicability than just vaccines.

The invention also provides a process for preparing a vaccine, comprising steps of: (i) preparing an emulsion as described above; and (ii) packaging the emulsion into a kit as a kit component together with an antigen component. The antigen and emulsion kit components can then be combined at a later time (e.g., at the point of use) for administration to a patient.

Carbonyl Components

Carbonyl components (e.g. formaldehyde, acetaldehyde and acetone) can arise as degradation products or residual impurities in various materials, such as polysorbate 80 and/or squalene. Their avoidance can be particularly important in pharmaceutical products, such as in emulsions where polysorbate 80 and/or squalene are present. These carbonyl components can react with other components in a composition (such as a protein) and thus their presence is undesirable. Acetaldehyde is of particular concern because, more than formaldehyde and acetone, its levels have been seen to rise during storage of oil-in-water emulsions which contain polysorbate 80 and squalene, due to degradation of these two compounds. If levels of acetaldehyde are already high in the starting materials then this degradation can mean that final levels at the time of use can be undesirably high.

Filtering polysorbate 80 prior to forming the oil-in-water emulsion has a beneficial effect. Thus the processes of the invention facilitate the production of oil-in-water emulsions which comprise less than 0.85 ppm acetaldehyde, e.g., less than 0.80 ppm, less than 0.75 ppm, less than 0.70 ppm, less than 0.65 ppm, less than 0.60 ppm, less than 0.55 ppm, less than 0.50 ppm, less than 0.45 ppm, less than 0.40 ppm, or even lower. The level in ppm is based on weight, such that 0.85 ppm means 0.85 μg acetaldehyde per gram of emulsion. By achieving this low level of acetaldehyde when the emulsion is first formed then its shelf life can be increased from about 3 years to about 5 years, under otherwise identical storage conditions.

The invention thus provides an oil-in-water emulsion comprising polysorbate 80, wherein the emulsion contains less than 0.85 ppm acetaldehyde, as discussed above. Methods for providing emulsions having such low levels of acetaldehyde have not previously been disclosed. The emulsion ideally comprises squalene, and further details on the emulsion are disclosed herein.

When stored, acetaldehyde levels in this emulsion can rise over time, but the low starting level and the polysorbate 80 filtration can ensure a long shelf-life with no more than 2.6 ppm acetaldehyde after 3 years storage at 4° C. (and, advantageously, even after 5 years). Thus, in a sixth aspect, the invention provides an oil-in-water emulsion comprising polysorbate 80, wherein the emulsion contains less than 2.6 ppm acetaldehyde after storage at 4° C. for at least 3 years, e.g., for 5 years.

Surfactants

Processes of the invention utilize at least one surfactant, i.e., one or more surfactants. Suitable surfactants include non-ionic surfactants. In some embodiments, the surfactant is a polymeric surfactant (i.e., it includes a polymeric group such as a polyoxyethylene or polyoxypropylene). In some embodiments, surfactants are non-ionic polymeric surfactants. In some embodiments, surfactants are non-ionic, polymeric ether surfactants. A preferred class of surfactants for use with the invention include at least one polyoxyethylene group, such as the poloxamers and polysorbates e.g. polysorbate 80 (commonly known by the trade name TWEEN™ 80).

Non-limiting examples of surfactants include TWEEN®20 (polysorbate 20), TWEEN®40 (polysorbate 40), TWEEN®60 (polysorbate 60), TWEEN®80 (polysorbate 80), TRITON™ X-100, IGEPAL CA-630, Nonidet P-40, PLURONIC® F-68, PLURONIC® F-88, and PLURONIC® F-127 (poloxamers), and Brij 35 (polyoxyethylene alkyl ether). The most preferred surfactant for use with the invention is polysorbate 80, which is a polyoxyethylene sorbitan ester surfactant also known as polyoxyethylene (20) sorbitan monooleate. It is available from a wide range of commercial manufacturers, including at pharmaceutical grade (e.g., the ultra-pure "Polysorbate (HX2)" product from NOF Corporation), and it is present in the "MF59" and "AS03" oil in-water emulsion vaccine adjuvants. It is generally supplied as a pure clear yellow/brown liquid.

Polysorbate 80 contains ether linkages and unsaturated alkyl chains that have been shown to auto-oxidize in aqueous solution, leading to reactive aldehydes including acetaldehyde which can cause undesirable side-reactions (e.g., by reacting with primary amino groups on proteins).

Thus the invention aims to reduce levels of acetaldehyde in polysorbate 80, and in emulsions which contain polysorbate 80, by utilising the filtration step disclosed herein. The filtered material is then used for preparing the oil in water emulsion, thereby providing final emulsions having reduced levels of acetaldehyde impurities.

During manufacture of oil in water emulsions with polysorbate 80 it is usual to disperse it in an aqueous carrier, and then to use this aqueous material to form the emulsion. Although the filtration step of the invention can be performed after polysorbate 80 has been mixed (diluted) with an aqueous carrier (e.g., w.f.i. or buffer), which may be used to reduce viscosity, it is preferred to filter the polysorbate 80 before such mixing occurs (i.e. it is performed on non-aqueous polysorbate 80); it may even be performed on anhydrous material (i.e., having substantially no water content), although the product specification for polysorbate 80 often permits up to 3 wt % water (which material is non-aqueous as it has no added water, but is not anhydrous). The filtered non-aqueous material can then be diluted with an aqueous carrier and used in the manner already known in the art (see below). It is also possible to mix non-aqueous polysorbate 80 with an aqueous carrier, then filter it, and then add further aqueous carrier to provide a final aqueous material ready for emulsification. Usually the material to be filtered is substantially free from any components other than the polysorbate 80 and any optional aqueous carrier, in which case the polysorbate 80 is not mixed with any component (except, optionally, the aqueous carrier) before being filtered.

Size Filtration of Surfactants

The invention utilizes a pre-filtration step for a surfactant. In some embodiments, such surfactant is a component of a product to be formulated. As discussed above, this pre-filtration step has been found to have a beneficial effect. By having a reduced initial acetaldehyde concentration the shelf-life of the adjuvant is thereby improved. Thus, filtration of a surfactant in accordance with the invention provides a purified surfactant.

The invention thus includes a prefiltration step for non-ionic surfactants, such as polysorbate 80. Filtration of the polysorbate 80 provides purified polysorbate 80 for use with the invention. The purified non-ionic surfactants, such as purified polysorbate 80, contain less than 0.85 ppm acetaldehyde. In some embodiments, a non-ionic surfactant prefiltered in accordance with the present invention contains no more than 0.85 ppm acetaldehyde, no more than 0.80 ppm acetaldehyde, no more than 0.75 ppm acetaldehyde, no more than 0.70 ppm acetaldehyde, no more than 0.65 ppm acetaldehyde, no more than 0.60 ppm acetaldehyde, no more than 0.55 ppm acetaldehyde, no more than 0.50 ppm acetaldehyde, no more than 0.45 ppm acetaldehyde, no more than 0.40 ppm acetaldehyde, no more than 0.35 ppm acetaldehyde, no more than 0.30 ppm acetaldehyde, no more than 0.25 ppm acetaldehyde, no more than 0.20 ppm acetaldehyde, or less.

As mentioned above, a surfactant to be filtered, e.g., polysorbate 80, can be mixed with water, to give aqueous surfactant, e.g., aqueous polysorbate 80, prior to filtration, but in some embodiments it is preferred to filter non-aqueous surfactant, e.g., non-aqueous polysorbate 80.

Filtration of surfactant, e.g., non-ionic surfactants such as polysorbate 80, utilizes a filter having a pore size which is between 5 μm and 50 μm, e.g., between 10-40 μm, between 10-30 μm, between 15-25 μm, between 18-22 μm, or about 20 μm. The pore size of a filter is assessed as the diameter of the largest glass particle which will pass through the filter under normal operating conditions.

In some embodiments, capsule filters are useful. Capsules include internal filtration membranes which provide a large surface area within a small volume to permit high throughput and flow rates.

Suitable filters include those formed from polypropylene fleece, polyethersulfone fleece, cellulose acetate, or glass fibre. Particularly useful filters include polypropylene fleece filters, e.g., a SARTOPURE™ PP 2 MIDICAP™ filter (which is available with pore size of 5 μm, 8 μm, 20 μm and 50 μm). A 20 μm polypropylene fleece filter may be particularly useful, such as the appropriate SARTOPURE™ PP 2 MIDICAP™ filter. This filter uses a 20 μm pleated polypropylene depth filter fleece material. Its 20 μm pore size is referred to by the manufacturer as its 'retention rate', and this filter's operating parameters permit a maximum allowable differential pressure of 5 bar at 20° C., with a maximum allowable back pressure of 2 bar.

It is known that filters often do not operate efficiently until a certain amount of sample has been processed. Monitoring of filtrate can be used to determine when the filter has settled down and is operating as desired. A SARTOPURE™ PP 2 MIDICAP™ 20 μm filter typically needs a flow of approximately 200 ml polysorbate 80 before it operates well, and so the first 200 ml or so of filtrate are generally discarded.

Typically, prefiltration of surfactant(s) in accordance with the present invention is carried out at room temperature (e.g., ambient condition), which is in the context of the invention defined as between about 14-25° C., more typically between about 18-22° C. In some embodiments, such prefiltration may be carried out at an elevated temperature, such as between about 26-45° C. A peristaltic pump may be used.

The filtered (purified) surfactant, e.g., filtered (purified) polysorbate 80, may be combined with an aqueous carrier to form an aqueous component which can then be used for subsequent step(s) of manufacture or formulation. For example, in cases of emulsion production, the filtered (purified) surfactant such as polysorbate 80 may be used for emulsification of an oil component and an aqueous component, so as to form an emulsion, e.g., oil-in-water emulsions and water-in-oil emulsions. Suitable aqueous carriers may be plain water (e.g., w.f.i.) or can include further components, e.g., solutes. For instance, it may include salts to form a buffer, e.g., citrate or phosphate salts, such as sodium salts. Typical buffers include: a phosphate buffer; a Tris buffer; a borate buffer; a succinate buffer; a histidine buffer; or a citrate buffer. Buffers will typically be included in the 5-50 mM range, but the skilled artisan may choose to use any suitable strength of buffers.

When the invention includes a step of post-filtration pre-emulsification mixing with an aqueous carrier, this mixing ideally uses an excess volume of aqueous carrier, e.g., at a volume ratio between 1:40 and 2:5 (e.g., from 1:20 to 1:5, 1:15 to 1:7, or about 1:10).

A surfactant will generally be used within 2 years of being filtered (i.e., prefiltered). Thus, for instance, if the surfactant is used to prepare an emulsion (as disclosed herein) then this can occur within 2 years of the filtration having occurred. In some embodiments it can be used after shorter durations, e.g., within 18 months, within 12 months, within 9 months, within 6 months, within 3 months, within 1 month, within 2 weeks, within 10 days, within 1 week, within 6 days, within 5 days, within 4 days, within 72 hours, within 60 hours, within 48 hours, within 24 hours or less. In some embodiments, a prefiltered surfactant that was stored longer than a certain duration may be re-filtered (i.e., repeated prefiltration) prior to being formulated into products of interest. For example, a prefiltered surfactant that has been stored longer than 2 years, 18 months, 12 months, 6 months, 3 months, 2 months, 1 month, 3 weeks, 2 weeks, 10 days, 1 week, 6 days, 5 days, 4 days, 72 hours, 60 hours, 48 hours, or 24 hours, may be filtered again prior to being formulated into a composition, such as emulsions.

According to the invention, compositions formulated with a surfactant processed as described herein exhibit enhanced stability. In some embodiments, the shelf-life of such compositions may be increased by at least 20%, e.g., at least 20%, at least 30%, at least 40%, at least 50%, at least 60%, at least 70%, at least 80%, at least 90%, at least 100%, or greater, as compared to negative control (i.e., equivalent counterpart that contains the same components but in which at least one surfactant is not pretreated in accordance with the present invention and is stored under the same condition).

Emulsions

Processes of the invention are also useful for the manufacture of emulsions, such as oil in water emulsions, water-in-oil emulsions, or water-in-oil-in-water emulsions. Thus, the invention provides methods for preparing an emulsion comprising at least one filtered (purified) surfactant (i.e., prefiltered prior to formulating into an emulsion). These emulsions, or products formulated with them, are particularly suitable for parenteral administration for pharmaceutical purposes e.g. vaccine adjuvants. These emulsions include at least three core ingredients: an oil component; an aqueous component; and a surfactant component.

In general, oil-in-water emulsions of the invention are formed by combining at least one oil (i.e., an oil component), an aqueous component such as water, and at least one surfactant which has been subjected to the methods described herein. Although spontaneous emulsification is possible, mixing will normally involve mechanical aid, such as the use of a homogenizer and/or a microfluidizer. A useful emulsification process mixes components first by using a homogenizer and then by using a microfluidizer. Where a component includes more than one compound (e.g., two different oils in the oil component, two different surfactants in the surfactant component, etc.), these may be combined in various orders prior to emulsification, e.g., a first surfactant and an oil may be pre-mixed, to be combined with a mixture of a second surfactant and an aqueous component.

Details of suitable oil component are discussed further below.

In some embodiments, emulsions of the invention comprise a non-ionic surfactant. In some embodiments, emulsions of the invention are oil-in-water emulsions which comprise a non-ionic surfactant. The terms "non-ionic" and "nonionic" are used interchangeably herein. In some embodiments, such oil-in-water emulsions comprise more than one surfactant, at least one of which is optionally a non-ionic surfactant which has been processed in accordance with the invention. In some embodiments, the surfactant component of an emulsion comprises a polysorbate which has been processed in accordance with the invention. In some embodiments, the surfactant component of an emulsion comprises polysorbate 80 which has been processed as discussed herein. Polysorbate 80 can be the sole surfactant in an emulsion of the invention, or it is possible to use multiple surfactants, i.e., comprising filtered polysorbate 80 and at least one further surfactant. For instance, "AS03" has polysorbate 80 as its sole surfactant component, whereas "MF59" uses a mixture of polysorbate 80 and sorbitan trioleate ("SPAN®85").

Surfactants can be classified by their "HLB" (hydrophile/lipophile balance), where an HLB in the range 1-10 generally means that the surfactant is more soluble in oil than in water, and an HLB in the range 10-20 are more soluble in water than in oil. Polysorbate 80 has a HLB of 15.0. If multiple surfactants are used then it will be usual to include a surfactant with an HLB value in the range of 1-10 (e.g., SPAN®85, with an HLB of 1.8). Surfactants which can be used in addition to polysorbate 80 include, but are not limited to: the polyoxyethylene sorbitan esters surfactants (commonly referred to as the Tweens), such as polysorbate 20; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-(TRITON™ X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); polyoxyethylene-9-lauryl ether; and sorbitan esters (commonly known as the SPANs), such as sorbitan trioleate (SPAN®85) and sorbitan monolaurate. A mixture of polysorbate 80 and sorbitan trioleate is particularly useful with the invention, e.g., at a 1:1 volume ratio.

Polysorbate 80 is biodegradable (metabolisable) and biocompatible; if further surfactant(s) is/are included then this/these may also be biodegradable and biocompatible.

The aqueous component comprises an aqueous solution which may be plain water (e.g., w.f.i.) or can include further components, e.g., solute(s). For instance, it may include salts to form a suitable buffer, e.g., citrate or phosphate salts, such as sodium salts. Typical buffers include, but are not limited to: a phosphate buffer, a Tris buffer, a borate buffer, a succinate buffer, a histidine buffer, and a citrate buffer. Buffers will typically be included in the 5-50 mM range, depending on the particular buffer being used.

In some embodiments, the total amount of oil(s) (% by volume) in the final emulsion is between about 1-25%, e.g., about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%. In some embodiments, the total amount of oil(s) (% by volume) in the final emulsion is between about 2-20%, between about 4-15%, between about 8-12%, for example, about 10%. When an emulsion comprises squalene as an oil component, a squalene content (% by volume) of between about 5% and about 10% is particularly useful, e.g., about 5%. In some embodiments, an emulsion comprises a squalene content (w/v) of between about 30-50 mg/ml, e.g., between about 35-45 mg/ml, about 36-43 mg/ml, about 38-40 mg/ml, etc.

In some embodiments, amounts of surfactants (% by weight) in the final emulsion are: polyoxyethylene sorbitan esters (such as TWEEN® 80) 0.02 to 2%, in particular about 0.5% or about 1% or about 2%; sorbitan esters (such as SPAN®85) 0.02 to 2%, in particular about 0.5% or about 1%; octyl- or nonylphenoxy polyoxyethanols (such as TRITON™ X-100) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%. A polysorbate 80 content (w/v) of between 4-6 mg/ml is useful, e.g., between 4.1-5.3 mg/ml, but higher levels are also useful, e.g., from 19-20 mg/ml. A sorbitan trioleate content (w/v) of between 4-6 mg/ml is useful, e.g., between 4.1-5.3 mg/ml.

The emulsion comprises polysorbate 80 and squalene and contains less than 0.85 ppm acetaldehyde.

Emulsions of the invention may be prepared in accordance with the techniques variously disclosed in References 10, 11 and 12 (the complete contents of each of which are incorporated herein by reference). Thus emulsification may involve formation of a first emulsion by homogenization, followed by microfluidization to provide a second emulsion. Components may be recirculated through the homogenizer and/or the microfluidiser using "type II" circulation [Reference 11], or a combination of "type I" and "type II" circulation. An inert atmosphere can be used during mixing. Temperature can be controlled around 40° C., for example, between about 35° C. and 45° C., e.g., about 35° C., about 36° C., about 37° C., about 38° C., about 38° C., about 40° C., about 41° C., about 42° C., about 43° C., about 44° C., and about 45° C. The emulsions can be filtered using a sterile asymmetric hydrophilic PES membrane. In some embodiments, the emulsions may be filtered using a sterile dual-layer (double-layer) 0.45 μm/0.22 μm asymmetric hydrophilic PES membrane filter.

Emulsions of the invention ideally have an average oil droplet diameter below 200 nm. In some embodiments, an average oil droplet of such emulsions has a diameter of, between about 50 nm and 200 nm, e.g., about 50 nm, about 60 nm, about 70 nm, about 800 nm, about 90 nm, about 100 nm, about 110 nm, about 120 nm, about 130 nm, about 140 nm, about 150 nm, about 160 nm, about 170 nm, about 180 nm, about 190 nm, and about 200 nm. In some embodiments, a diameter of oil droplets that is 155±20 nm is typical, and it will generally not be less than 50 nm. The average diameter (i.e., the number average diameter of the emulsion's oil droplets) may be measured using a dynamic light scattering technique, as described for example in Reference 13. An example of a dynamic light scattering measurement machine is the Nicomp 380 Submicron Particle Size Analyzer (from Particle Sizing Systems).

In some embodiments, surfactants processed by the methods of the present invention are useful for producing uniform emulsions, e.g., uniform oil-in-water emulsions and uniform water-in-oil emulsions. Uniformity of an emulsion refers to having fewer oil droplets that fall outside of a preferred size range within a population of oil droplets. In some embodiments, a uniform oil-in-water emulsion that incorporates at least one surfactant processed by the methods of the invention contains ≤5% (e.g., ≤4%, ≤3%, ≤2% and ≤1%) of the number of oil droplets that fall outside of a preferred range of diameters. In some embodiments, a uniform oil-in-water emulsion that incorporates at least one surfactant processed by the methods of the invention is characterized in that the number of oil droplets in a population (e.g., preparation) having a diameter of >1.2 μm is $5\times10^8$/mL or less, e.g., $5\times10^8$/mL or less, $5\times10^7$/mL or less, $5\times10^6$/mL or less, and $5\times10^5$/mL or less.

Methods provided herein may be used at large scale, suitable for commercial-scale production of a composition comprising a surfactant that has been prefiltered according to the methods embraced in the present application. Thus a method may involve preparing a final emulsion with a volume greater than 1 liter, e.g., >5 liters, >10 liters, >20 liters, >50 liters, >100 liters, >250 liters, etc.

The process is particularly useful for preparing any of the following exemplary oil-in-water emulsions:

An Emulsion Comprising Squalene, Polysorbate 80 (TWEEN® 80), and Sorbitan Trioleate (SPAN®85):

The composition of the emulsion by volume can be about 5% squalene, about 0.5% polysorbate 80 and about 0.5% sorbitan trioleate. In weight terms, these amounts become 4.3% squalene, 0.5% polysorbate 80 and 0.48% sorbitan trioleate. This adjuvant is known as "MF59." The MF59 emulsion may advantageously include citrate ions, e.g., 10 mM sodium citrate buffer. In some embodiments, the final concentration of each of such components present in a product may be halved, e.g., about 2.5% squalene, about 0.25% polysorbate 80 and about 0.25% sorbitan trioleate by volume (about 2.15% squalene, 0.25% polysorbate 80 and 0.24% sorbitan trioleate in weight terms). In some embodiments, the final concentration of each of such components present in a product may be quartered, e.g., about 1.25% squalene, about 0.125% polysorbate 80 and about 0.125% sorbitan trioleate by volume (about 1.075% squalene, 0.125% polysorbate 80 and 0.12% sorbitan trioleate in weight terms).

As described in Reference 14, MF59 is manufactured on a commercial scale by dispersing SPAN®85 in the squalene phase (the oil component) and TWEEN® 80 in the aqueous component, followed by high-speed mixing to form a coarse emulsion (i.e., first emulsion). This coarse emulsion is then passed through a microfluidizer to produce an emulsion having a uniform oil droplet size (i.e., second emulsion). As described in Reference 6, the microfluidized emulsion is then filtered through a suitable membrane filter in order to remove any large oil droplets, and the mean droplet size of the resulting uniform emulsion remains unchanged for at least 3 years at 4° C. The squalene content of the final emulsion can be measured as described in Reference 15.

An Emulsion Comprising Squalene, an α Tocopherol (Ideally DL α Tocopherol), and Polysorbate 80:

The emulsion may include phosphate buffered saline. These emulsions may have by volume from 2 to 10% squalene, from 2 to 10% tocopherol and from 0.3 to 3% polysorbate 80, e.g., 4.3% squalene, 4.7% α tocopherol, 1.9% polysorbate 80. The weight ratio of squalene:tocopherol is preferably <1 (e.g., 0.90) as this can provide a more stable emulsion. Squalene and polysorbate 80 may be present volume ratio of about 5:2 or at a weight ratio of about 11:5. Thus the three components (squalene, tocopherol, polysorbate 80) may be present at a weight ratio of 1068:1186:485 or around 55:61:25. One such emulsion ("AS03" [Reference 16]) has 4.86 mg polysorbate 80, 10.69 mg squalene and 11.86 mg α tocopherol per dose (or a fraction thereof, but maintaining the mass ratios), e.g., in a 0.5 ml volume. AS03 can be made by dissolving TWEEN® 80 in PBS to give a 2% solution, then mixing 90 ml of this solution with a mixture of (5 g of DL α-tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d MPL). Another useful emulsion of this type may comprise, per human dose, 0.5-10 mg squalene, 0.5-11 mg tocopherol, and 0.1-4 mg polysorbate 80 [Reference 17], e.g., in the ratios discussed above.

An Emulsion Comprising Squalene, Polysorbate 80, a Triton Detergent (e.g., Triton X 100) and a Tocopherol (e.g., an α-Tocopherol Succinate):

The emulsion may include these three components at a mass ratio of about 75:11:10 (e.g., 750 μg/ml polysorbate 80, 110 μg/ml Triton X-100 and 100 μg/ml α-tocopherol succinate), and these concentrations should include any contribution of these components from antigens. The emulsion may also include a 3d MPL. The emulsion may also include a saponin, such as QS21. The aqueous component may contain a phosphate buffer.

The compositions of these emulsions, expressed above in percentage terms, may be modified by dilution or concentration (e.g., by an integer, such as 2 or 3 or by a fraction, such as ⅔ or ¾), in which their ratios stay the same. For instance, a 2-fold concentrated MF59 would have about 10% squalene, about 1% polysorbate 80 and about 1% sorbitan trioleate. Concentrated forms can be diluted (e.g., with an antigen solution) to give a desired final concentration of emulsion.

Emulsions of the invention are ideally stored at between 2° C. and 8° C. They should not be frozen. They should ideally be kept out of direct light. In particular, squalene-containing compositions, such as emulsions and vaccines of the invention should be protected to avoid photochemical breakdown of squalene. If emulsions of the invention are stored then this is preferably in an inert atmosphere, e.g., $N_2$ or argon.

Oil Component

Because emulsions that contain at least one surfactant processed by the methods of the invention are intended to include pharmaceutical use, in such embodiments, the oil(s) in the emulsion's oil component will typically be biodegradable (metabolisable) and biocompatible.

As discussed above, the invention is particularly suitable for use in preparing emulsions which include squalene. Squalene is a naturally occurring oil (for example in shark liver) which is a branched, unsaturated terpenoid ($C_{30}H_{50}$; $[(CH_3)_2C{=}CHCH_2CH_2C(CH_3)]_2{=}CHCH_2{-}]_2$; 2,6,10,15,19,23-hexamethyl-2,6,10,14,18,22-tetracosahexaene; CAS RN 7683-64-9). Squalene is typically purified from animal sources, such as shark, but it is also possible to use squalene from non-animal sources, e.g., genetically-engineered yeasts [Reference 18] and vegetable oils such as olive oil [References 19, 20]. Further possible sources include wheat germ oil, palm oil, amaranth seed (e.g., see Reference 21), and rice bran oil. It can be purified by distillation, e.g., as disclosed in Reference 22.

The oil component in an emulsion of the invention may include a single oil, or may comprise a combination of oils, e.g., comprising squalene and at least one further oil. For instance, "MF59" has squalene as its sole oil component, whereas "AS03" has squalene and α-tocopherol.

Rather than (or on addition to) using squalene an emulsion can comprise oil(s) including those from, for example, an animal (such as fish) or a vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and so may be used. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Squalane, the saturated analog to squalene, can also be used. Fish oils, including squalene and squalane, are readily available from commercial sources or may be obtained by methods known in the art.

Other useful oils are the tocopherols, particularly in combination with squalene. Where the oil component of an emulsion includes a tocopherol, any of the α, β, γ, δ, ε or ξ tocopherols can be used, but α tocopherols are preferred. D α tocopherol and DL α tocopherol can both be used. A preferred α tocopherol is DL α tocopherol. The tocopherol can take several forms, e.g. different salts and/or isomers. Salts include organic salts, such as succinate, acetate, nicotinate, etc. If a salt of this tocopherol is to be used, the preferred salt is the succinate. An oil combination comprising squalene and a tocopherol (e.g. DL α-tocopherol) is particularly useful with the invention.

Where the invention utilises shark-derived squalene, any suitable shark species can be used, such as the spiny dogfish (*Squalus acanthias*). Other suitable species include *Centrophorus atromarginatus, Cetorhinus maximus, Echinorhinus brucus, Scymnodon squamulosus, Centrophorus atromarginatus, Etmopterus frontimaculatus, Deania eglantine* and *Scymnodon foliaceus*.

As discussed in Reference 23, when using shark-derived squalene it is preferred that polychlorinated biphenyls (PCBs) are present at a level of less than 661 pg PCBs per g squalene (TEQ). This 661 pg/g limit can be applied to the squalene used to make an emulsion, to the final emulsion, and to a vaccine made using the emulsion. Usually it applies to the squalene used to make an emulsion. Full details of how to achieve a PCB level within this threshold are found in Reference 23. Levels much lower than 661 pg/g can be achieved, even as low as ~2 pg/g.

PCBs are a family of chemical compounds formed by the addition of chlorine to the 10 positions available for chlorine substitution in a biphenyl ring. Any single chemical compound in the PCB category is called a "congener." Levels of individual congeners are converted to a toxic equivalent (TEQ) which allows the toxicity of a mixture of PCBs to be represented as a single number. The toxicity of each PCB is expressed as a fraction (the toxic equivalency factor, TEF) of the toxicity of 2,3,7,8-TCDD dioxin (which has a reference value of 1). To calculate the total TEQ of a mixture, the mass of each PCB is multiplied by its TEF and then the TEQ is the sum of these values.

In some embodiments the squalene has, in addition to a TEQ as above, no detectable amounts of one or more of: PCB #126; PCB #169; PCB #77; PCB #81; PCB #123; PCB #170; and/or PCB #180. These PCBs are defined by IUPAC nomenclature e.g. PCB #126 is 3,3',4,4',5-pentachlorobiphenyl.

As well as having a low PCB content, it is useful to ensure low dioxin levels. Thus each of the following may have a low dioxin content: squalene used to form emulsions; the final pharmaceutical emulsion; and a vaccine made using the emulsion. A low dioxin content is less than 1 ng per gram of squalene, and preferably less than 1 pg/g (TEQ).

Similarly it is useful to ensure low furan levels. Thus each of the following may have a low furan content: squalene used to form emulsions of the invention; the final pharmaceutical emulsion; and a vaccine made using the emulsion of the invention. A low furan content is less than 1 ng per gram of squalene, and preferably <1 pg/g (TEQ).

Vaccines

Although it is possible to administer oil in water emulsion adjuvants on their own to patients (e.g., to provide an adjuvant effect for an antigen that has been separately administered to the patient), it is more usual to admix the adjuvant with an antigen prior to administration, to form an immunogenic composition, e.g., a vaccine. Mixing of emulsion and antigen may take place extemporaneously, at the time of use, or can take place during vaccine manufacture, prior to filling. The methods of the invention can be applied in both situations.

Thus a process of the invention may include a further process step of admixing the emulsion with an antigen component. As an alternative, it may include a further step of packaging the adjuvant into a kit as a kit component together with an antigen component.

Overall, therefore, the invention can be used when preparing mixed vaccines or when preparing kits including antigen and adjuvant ready for mixing. Where mixing takes place during manufacture then the volumes of bulk antigen and emulsion that are mixed will typically be greater than 1 liter, e.g., >5 liters, >10 liters, >20 liters, >50 liters, >100 liters, >250 liters, etc. Where mixing takes place at the point of use then the volumes that are mixed will typically be smaller than 1 milliliter, e.g., <0.6 ml, <0.5 ml, <0.4 ml, <0.3 ml, <0.2 ml, etc. In both cases it is usual for substantially equal volumes of emulsion and antigen solution to be mixed i.e. substantially 1:1 (e.g., between 1.1:1 and 1:1.1, preferably between 1.05:1 and 1:1.05, and more preferably between 1.025:1 and 1:1.025). In some embodiments, however, an excess of emulsion or an excess of antigen may be used [Reference 24]. Where an excess volume of one component is used, the excess will generally be at least 1.5:1, e.g., >2:1, >2.5:1, >3:1, >4:1, >5:1, etc.

Where antigen and adjuvant are presented as separate components within a kit, they are physically separate from each other within the kit, and this separation can be achieved in various ways. For instance, the components may be in separate containers, such as vials. The contents of two vials can then be mixed when needed, e.g., by removing the contents of one vial and adding them to the other vial, or by separately removing the contents of both vials and mixing them in a third container.

In another arrangement, one of the kit components is in a syringe and the other is in a container such as a vial. The syringe can be used (e.g., with a needle) to insert its contents into the vial for mixing, and the mixture can then be withdrawn into the syringe. The mixed contents of the syringe can then be administered to a patient, typically through a new sterile needle. Packing one component in a syringe eliminates the need for using a separate syringe for patient administration.

In another preferred arrangement, the two kit components are held together but separately in the same syringe, e.g., a dual chamber syringe. When the syringe is actuated (e.g., during administration to a patient) then the contents of the two chambers are mixed. This arrangement avoids the need for a separate mixing step at time of use.

The contents of the various kit components will generally all be in liquid form. In some arrangements, a component (typically the antigen component rather than the emulsion component) is in dry form (e.g., in a lyophilized form), with the other component being in liquid form. The two components can be mixed in order to reactivate the dry component and give a liquid composition for administration to a patient. A lyophilized component will typically be located within a vial rather than a syringe. Dried components may include stabilizers such as lactose, sucrose or mannitol, as well as mixtures thereof, e.g., lactose/sucrose mixtures, sucrose/mannitol mixtures, etc. One possible arrangement uses a liquid emulsion component in a pre-filled syringe and a lyophilized antigen component in a vial.

If vaccines contain components in addition to emulsion and antigen then these further components may be included in one these two kit components, or may be part of a third kit component.

Suitable containers for mixed vaccines of the invention, or for individual kit components, include vials and disposable syringes. These containers should be sterile.

Where a composition/component is located in a vial, the vial is preferably made of a glass or plastic material. The vial is preferably sterilized before the composition is added to it. To avoid problems with latex sensitive patients, vials are preferably sealed with a latex-free stopper, and the absence of latex in all packaging material is preferred. In one embodiment, a vial has a butyl rubber stopper. The vial may include a single dose of vaccine/component, or it may include more than one dose (a "multidose" vial), e.g., 10 doses. In one embodiment, a vial includes 10×0.25 ml doses of emulsion. Preferred vials are made of colorless glass.

A vial can have a cap (e.g., a Luer lock) adapted such that a pre filled syringe can be inserted into the cap, the contents of the syringe can be expelled into the vial (e.g., to reconstitute lyophilized material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed.

Where a composition/component is packaged into a syringe, the syringe will not normally have a needle attached to it, although a separate needle may be supplied with the syringe for assembly and use. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield.

The emulsion may be diluted with a buffer prior to packaging into a vial or a syringe. Typical buffers include: a phosphate buffer; a Tris buffer; a borate buffer; a succinate buffer; a histidine buffer; or a citrate buffer. Dilution can reduce the concentration of the adjuvant's components while retaining their relative proportions, e.g., to provide a "half-strength" adjuvant.

Containers may be marked to show a half dose volume, e.g., to facilitate delivery to children. For instance, a syringe containing a 0.5 ml dose may have a mark showing a 0.25 ml volume.

Where a glass container (e.g., a syringe or a vial) is used, then it is preferred to use a container made from a borosilicate glass rather than from a soda lime glass.

Various antigens can be used with oil in water emulsions, including but not limited to: viral antigens, such as viral surface proteins; bacterial antigens, such as protein and/or saccharide antigens; fungal antigens; parasite antigens; and tumor antigens. The invention is particularly useful for vaccines against influenza virus, HIV, hookworm, hepatitis B virus, herpes simplex virus, rabies, respiratory syncytial virus, cytomegalovirus, *Staphylococcus aureus*, *chlamydia*, SARS coronavirus, varicella zoster virus, *Streptococcus pneumoniae*, *Neisseria meningitidis*, *Mycobacterium tuberculosis*, *Bacillus anthracis*, Epstein Barr virus, human papillomavirus, etc. Preferably the antigen is an influenza virus antigen. Non-limiting examples of suitable antigens are further provided below.

Influenza Virus Antigens:

These may take the form of a live virus or an inactivated virus. Where an inactivated virus is used, the vaccine may comprise whole virion, split virion, or purified surface antigens (including hemagglutinin and, usually, also including neuraminidase). Influenza antigens can also be presented in the form of virosomes. The antigens may have any hemagglutinin subtype, selected from H1, H2, H3, H4, H5, H6, H7, H8, H9, H10, H11, H12, H13, H14, H15 and/or H16. Vaccine may include antigen(s) from one or more (e.g., 1, 2, 3, 4 or more) influenza virus strains, including influenza A virus and/or influenza B virus, e.g., a monovalent A/H5N1 or A/H1N1 vaccine, or a trivalent A/H1N1+A/H3N2+B vaccine. The influenza virus may be a reassortant strain, and may have been obtained by reverse genetics techniques [e.g., References 25-29]. Thus the virus may include one or more RNA segments from a A/PR/8/34 virus (typically 6 segments from A/PR/8/34, with the HA and N segments being from a vaccine strain, i.e., a 6:2 reassortant). The viruses used as the source of the antigens can be grown either on eggs (e.g., embryonated hen eggs) or on cell culture. Where cell culture is used, such host cells will typically be an eukaryotic host/cell, e.g., mammalian cells, avian cells, insect cells, plant cells and yeast cells. In some embodiments, suitable host cells are embryonic stem cells. In some embodiments, suitable host cells are of epithelial origin. In some embodiments, suitable host cells are kidney cells.

Suitable mammalian cell lines include, but not limited to: MDCK; CHO; 293T; BHK; Vero; MRC 5; PER.C6; WI-38; etc. Suitable avian cell lines include, but not limited to: EB66® cells. Preferred mammalian cell lines for growing influenza viruses include: MDCK cells [References 30-33], derived from Madin Darby canine kidney; Vero cells [References 34-36], derived from African green monkey kidney; or PER.C6 cells [Reference 37], derived from human embryonic retinoblasts. Where virus has been grown on a mammalian cell line then the composition will advantageously be free from egg proteins (e.g., ovalbumin and ovomucoid) and from chicken DNA, thereby reducing allergenicity. Unit doses of vaccine are typically standardized by reference to hemagglutinin (HA) content, typically measured by SRID. Existing vaccines typically contain about 15 µg of HA per strain, although lower doses can be used, particularly when using an adjuvant. Fractional doses such as ½ (i.e., 7.5 µg HA per strain), ¼ and ⅛ have been used [References 38, 39], as have higher doses (e.g., 3× or 9× doses [References 40, 41]). Thus vaccines may include between 0.1 and 150 µg of HA per influenza strain, preferably between 0.1 and 50 µg, e.g., 0.1-20 µg, 0.1 15 µg, 0.1 10 µg, 0.1 7.5 µg, 0.5-5 µg, etc. Particular doses include, e.g., about 15, about 10, about 7.5, about 5, about 3.8, about 3.75, about 1.9, about 1.5 µg of HA, etc. per strain.

Human Immunodeficiency Virus:

Suitable antigens include those derived from HIV 1 and HIV 2. The antigen will typically be an envelope antigen.

Hepatitis B Virus Surface Antigens:

This antigen is preferably obtained by recombinant DNA methods, e.g., after expression in a *Saccharomyces cerevisiae* yeast. Unlike native viral HBsAg, the recombinant yeast-expressed antigen is non-glycosylated. It can be in the form of substantially-spherical particles (average diameter of about 20 nm), including a lipid matrix comprising phospholipids. Unlike native HBsAg particles, the yeast-expressed particles may include phosphatidylinositol. The HBsAg may be from any of subtypes ayw1, ayw2, ayw3, ayw4, ayr, adw2, adw4, adrq– and adrq+.

Hookworm:

Suitable hookworm antigens include those particularly as seen in canines (*Ancylostoma caninum*). Such antigen may be recombinant Ac-MTP-1 (astacin-like metalloprotease) and/or an aspartic hemoglobinase (Ac APR 1), which may be expressed in a suitable host expression system, such as baculovirus/insect cell system as a secreted protein [References 42, 43].

Herpes Simplex Virus Antigens (HSV):

A preferred HSV antigen for use with the invention is membrane glycoprotein gD. It is preferred to use gD from a HSV 2 strain ("gD2" antigen). The composition can use a form of gD in which the C terminal membrane anchor region has been deleted [Reference 44], e.g., a truncated gD comprising amino acids 1 306 of the natural protein with the addition of aparagine and glutamine at the C-terminus. This form of the protein includes the signal peptide which is cleaved to yield a mature 283 amino acid protein. Deletion of the anchor allows the protein to be prepared in soluble form.

Human Papillomavirus Antigens (HPV):

Preferred HPV antigens for use with the invention are L1 capsid proteins, which can assemble to form structures known as virus-like particles (VLPs). The VLPs can be produced by recombinant expression of L1 in yeast cells (e.g., in *S. cerevisiae*) or in insect cells (e.g., in *Spodoptera* cells, such as *S. frugiperda*, or in *Drosophila* cells). For yeast cells, plasmid vectors can carry the L1 gene(s); for insect cells, baculovirus vectors can carry the L1 gene(s). More preferably, the composition includes L1 VLPs from both HPV-16 and HPV-18 strains. This bivalent combination has been shown to be highly effective [Reference 45]. In addition to HPV 16 and HPV 18 strains, it is also possible to include L1 VLPs from HPV 6 and HPV 11 strains. The use of oncogenic HPV strains is also possible. A vaccine may include between 20-60 µg/ml (e.g., about 40 µg/ml) of L1 per HPV strain.

Anthrax Antigens:

Anthrax is caused by *Bacillus anthracis*. Suitable *B. anthracis* antigens include A-components (lethal factor (LF) and edema factor (EF)), both of which can share a common B-component known as protective antigen (PA). The antigens may optionally be detoxified. Further details can be found in the literature, e.g., [References 46-48].

*S. aureus* Antigens:

A variety of *S. aureus* antigens are known. Suitable antigens include capsular saccharides (e.g., from a type 5 and/or type 8 strain) and proteins (e.g., IsdB, Hla, etc.). Capsular saccharide antigens are ideally conjugated to a carrier protein.

*S. pneumoniae* Antigens:

A variety of *S. pneumoniae* antigens are known. Suitable antigens include capsular saccharides (e.g., from one or more of serotypes 1, 4, 5, 6B, 7F, 9V, 14, 18C, 19F, and/or 23F) and proteins (e.g., pneumolysin, detoxified pneumolysin, polyhistidine triad protein D (PhtD), etc.). Capsular saccharide antigens are ideally conjugated to a carrier protein.

A solution of the antigen will normally be mixed with the emulsion, e.g., at a 1:1 volume ratio. This mixing can either be performed by a vaccine manufacturer, prior to filling, or can be performed at the point of use, by a healthcare worker.

Pharmaceutical Compositions

Compositions made using a surfactant processed by the methods of the invention include pharmaceutical, nutraceutical and cosmetic compositions. The invention is not limited by a particular type of products, provided that it is desirable to use one or more surfactants prepared in accordance with the methods provided herein to formulate such products. In some embodiments, such products exhibit higher quality (e.g., improved purity, stability, shelf life, or any combination thereof), as compared to a reference counterpart (control), which contains equivalent components or ingredients with the exception of one or more surfactants not subjected to the methods described herein (e.g., prefiltration). Thus, in some embodiments, the compositions comprising one or more surfactants prepared in accordance with the invention contain lower levels of carbonyl impurities, as compared to the reference counterpart (control).

In some embodiments, such compositions of the present invention are pharmaceutically acceptable. In relation to vaccines for immunization, a composition may include one or more additional components, such as an antigen. In some embodiments, such immunization is carried out in conjunction with the use of an adjuvant, e.g., oil-in-water adjuvants. Thus, such vaccines may contain an emulsion-based adjuvant, which may include at least one surfactants processed in accordance with the methods described herein, and an optional antigen.

The composition may include a preservative such as thiomersal or 2-phenoxyethanol. It is preferred, however, that such a composition should be substantially free from (i.e., less than 5 µg/ml) mercurial material e.g., thiomersal-free [References 49, 50]. Compositions and components containing no mercury are more preferred. For example, preservative-free vaccines are also useful.

The pH of a composition will generally be between 5.0 and 8.1, and more typically between 6.0 and 8.0, e.g., between 6.5 and 7.5. A process of the invention may therefore include a step of adjusting the pH of the composition prior to packaging.

The composition is preferably sterile. The composition is preferably non pyrogenic, e.g., containing <1 EU (endotoxin unit, a standard measure) per dose, and preferably <0.1 EU per dose. The composition is preferably gluten free.

The invention includes kits and compositions prepared using the methods of the invention. In some embodiments, such compositions are prophylactic compositions, such as vaccines. In any of the embodiments, pharmaceutical compositions comprising a surfactant processed by the methods provided herein may provide improved stability (e.g., longer shelf life) as compared to equivalent compositions comprising the same surfactant but not processed in accordance with the invention.

The composition may include material for a single administration immunization, or may include material for multiple administrations immunizations (i.e., a "multidose" kit). Where the composition is a vaccine for immunization, the vaccine may include material for a single immunization or may include material for multiple immunizations (i.e., a "multidose" kit). In some embodiments, the inclusion of a preservative may be preferred in multidose arrangements.

Compositions containing one or more surfactants processed by the methods disclosed herein may be filled in sterile closed systems. Suitable sterile closed systems include, but are not limited to: vials, syringes (such as disposable syringes), glass and plastic containers, including rigid or flexible containers (e.g., bags). In some embodiments, a sterile closed system suitable for use in the present disclosure is coated for surface-modified, e.g., siliconized.

Methods of Treatment, and Administration of the Pharmaceutical Composition

The compositions prepared according to the methods of the invention are suitable for administration to subjects, including human patients. Pharmaceutical compositions comprising a surfactant processed by the methods provided herein are suitable for administration to a subject in need thereof. In some embodiments, such a composition is a therapeutic composition that is administered to a subject for the treatment of disease or disorder, wherein the composition comprises a suitable active ingredient intended for the treatment. In some embodiments, the immune response is elicited in order to provide therapeutic effects, prophylactic effects, or both. In some embodiments, the immune response is elicited in order to provide therapeutic effects. In some embodiments, the immune response is elicited in order to provide prophylactic effects, for example, as a vaccine. In some embodiments, such immune response is augmented by the presence of at least one adjuvant.

In some embodiments, the invention provides a method of raising an immune response in a patient, comprising the step of administering to the patient a composition of the invention which includes an immunogen, so as to enhance an immune response.

Pharmaceutical compositions prepared according to the invention may be used to treat a subject (e.g., patients) in need thereof, including children and adults, who meet certain criteria, such as clinical criteria, genetic criteria, risk factors, age groups, etc. The patient may be less than 1 year old, 1-5 years old, 5-15 years old, 15-55 years old, or at least 55 years old. The patient may be elderly (e.g., >50 years old, preferably >65 years), the young (e.g., <5 years old), hospitalized patients, healthcare workers, armed service and military personnel, pregnant women, the chronically ill, immunodeficient or immunocompromised patients, and people travelling abroad. Where pharmaceutical compositions are prophylactic vaccines for immunization, such vaccines are suitable not solely for these groups, however, but may be used more generally in a population, e.g., healthy subjects.

Vaccines of the invention may be administered to patients at substantially the same time as (e.g., during the same medical consultation or visit to a healthcare professional) other vaccines.

The compositions can be administered in any suitable way, including, but not limited to: intramuscular injection (e.g., into the arm or leg), subcutaneous injection, intranasal [References 51-53], oral [Reference 54], intradermal [References 55, 56], transcutaneous, transdermal [Reference 57], etc.

Pharmaceutical compositions, including vaccines, are typically administered in a dosage volume of about 0.5 ml, although a half dose (e.g., about 0.25 ml) may be administered to children. However, administration volumes are readily adjusted by the person skilled in the art to suit the particular use or purpose.

The invention also provides these kits and compositions for use as medicaments.

The invention also provides the use of: (i) an aqueous preparation of an antigen or a therapeutic protein or peptide; and (ii) an oil in water emulsion comprising a surfactant prepared according to the invention, in the manufacture of a medicament for administering to a patient.

The immune response raised by these methods and uses will generally include an antibody response, preferably a protective antibody response.

General

Throughout the specification, including the claims, where the context permits, the term "comprising" and variants thereof such as "comprises" are to be interpreted as including the stated element (e.g., integer) or elements (e.g., integers) without necessarily excluding any other elements (e.g., integers). Thus a composition "comprising" X may consist exclusively of X or may include something additional, e.g., X+Y.

The word "substantially" does not exclude "completely," e.g., a composition which is "substantially free" from Y may be completely free from Y. Where necessary, the word "substantially" may be omitted from the definition of the invention. In some embodiments, "a composition that is substantially free of a component" may include such a composition with a residual amount of the component, wherein the residual amount is (i) below reliable detection levels by suitable or art-accepted measurement means; and/or (ii) the residual amount does not adversely affect an intended purpose of the composition.

The term "about" in relation to a numerical value x is optional and means, for example, x+10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal derived materials.

Accordingly, the following embodiments are conceivable from the above and the examples:

A1. A bulk preparation of a surfactant, characterized in that the surfactant contains fewer aggregates than the surfactant not subjected to prefiltration with a filter having a pore size of between 5-50 µm;
wherein the surfactant is a nonionic surfactant; and,
wherein the bulk preparation has a volume of at least 10 liters.

A2. The bulk preparation of embodiment A1, wherein the surfactant is an anhydrous surfactant.

A3. The bulk preparation of any one of the preceding embodiments, having a volume of at least 20 liters, 50 liters, at least 100 liters, at least 125 liters, at least 150 liters, at least 175 liters, at least 200 liters, at least 250 liters, or at least 300 liters.

A4. The bulk preparation of any one of the preceding embodiments, characterized in that the bulk preparation of a surfactant contains a carbonyl level that is lower than that of the surfactant not subjected to the pre-filtration.

A5. The bulk preparation of any one of the preceding embodiments, wherein the nonionic surfactant is selected from the group consisting of:
TWEEN®20 (polysorbate 20), TWEEN®40 (polysorbate 40), TWEEN®60 (polysorbate 60), TWEEN®80 (polysorbate 80), TRITON™ X-100, IGEPAL CA-630, Nonidet P-40, PLURONIC® F-68, PLURONIC® F-88, and PLURONIC® F-127 (poloxamers), and Brij 35 (polyoxyethylene alkyl ether).

A6. A liquid composition comprising an aqueous component and a pre-filtered surfactant,
wherein the pre-filtered surfactant is obtained from the bulk preparation of any one of the preceding embodiments.

A7. The liquid composition of embodiment A6, further comprising an oil component.

A8. The liquid composition of embodiment A6 or A7, wherein the liquid composition is an emulsion.

A9. The liquid composition of embodiment A8, wherein the liquid composition is an oil-in-water emulsion or a water-in-oil emulsion.

A10. The liquid composition of embodiment A7, wherein the oil component is selected from the group consisting of:
saturated fatty acids, unsaturated fatty acids, short-chain fatty acids, medium-chain fatty acids, long-chain fatty acids, very long-chain fatty acids, and sterol precursors.

A11. The liquid composition of embodiment of embodiment A10, wherein the oil component is or comprises squalene.

A12. The liquid composition of embodiment A6, wherein the liquid composition comprises a surfactant selected from the group consisting of polysorbates.

A13. The liquid composition of embodiment A12, wherein the surfactant is polysorbate 80.

A14. A method for preparing the liquid composition, the method comprising the steps of:
pre-filtering a surfactant with a filter having an average pore size of 5-50 micron at room temperature so as to form a pre-filtered surfactant; and,
combining the pre-filtered surfactant with an aqueous component so as to form the liquid composition of any one of embodiments A6-A13.

A15. A method for preparing the liquid composition, the method comprising the steps of:
providing a prefiltered surfactant according to any one of embodiments A1-A5; and,
combining the pre-filtered surfactant with an aqueous component so as to form the liquid composition of any one of embodiments A6-A13.

A16. The method of embodiment A14 or A15, wherein the liquid composition is a pharmaceutical composition comprising at least one API.

A17. The method of embodiment A16, wherein the liquid composition further comprises an oil component.

A18. The method of embodiment A16 or A17, further comprising the steps of:
emulsifying the liquid composition so as to form a first emulsion;
subjecting the first emulsion to high shear force and high pressure so as to form a second emulsion; and,
filtering the second emulsion, so as to form a uniform emulsion.

A19. The method of embodiment A18, wherein the first emulsion is characterized in that a first average oil droplet size is 5000 nm or less, and wherein the number of oil droplets having a size of >1.2 µm in the first emulsion is $5 \times 10^{11}$/ml or less.

A20. The method of embodiment A18 or A19, wherein the second emulsion is characterized in that a second average oil droplet size is 500 nm or less, and wherein the number of oil droplets having a size of >1.2 µm in the second emulsion is $5 \times 10^{10}$/ml or less.

A21. The method of any one of embodiments A18-A20, wherein the uniform emulsion is characterized in that a third average oil droplet size is between about 80 and 220 nm, and wherein the number of oil droplets having a size of >1.2 µm in the uniform emulsion is $5 \times 10^{8}$/ml or less.

A22. The method of embodiment A21, wherein the uniform emulsion comprises squalene, polysorbate 80 and sorbitan trioleate.

A23. The method of embodiment A22, wherein the uniform emulsion comprises about 4.3% squalene, about 0.5% polysorbate 80 and about 0.48% sorbitan trioleate by weight.

Specifically, the present invention relates to the following embodiments:

B1. A process for preparing an oil-in-water emulsion comprising steps of: (a) filtering polysorbate 80 through a filter having a pore size between 5-50 µm, to provide purified polysorbate 80; and (b) combining the purified polysorbate 80 with an oil component to provide the emulsion.

B2. The process of embodiment B1, wherein step (a) comprises: filtering non-aqueous polysorbate 80 through a polypropylene filter having a pore size between 5-50 µm.

B3. The process of any preceding embodiment, wherein the purified polysorbate 80 is combined with an aqueous material between steps (a) and (b).

B4. The process of any preceding embodiment, wherein step (b) comprises homogenization to form a homogenized emulsion.

B5. The process of any preceding embodiment, wherein step (b) comprises microfluidization to form a microfluidized emulsion.

B6. The process of embodiment B4 or embodiment B5, wherein step (b) comprises sterile filtration of the homogenized or microfluidized emulsion.

B7. The process of any preceding embodiment, wherein the oil-in-water emulsion is a vaccine adjuvant including squalene.

B8. The process of embodiment B7, wherein the oil-in-water emulsion comprises squalene, the polysorbate 80, and sorbitan trioleate, e.g. 5% squalene, 0.5% polysorbate 80 and 0.5% sorbitan trioleate (by volume).

B9. The process of any preceding embodiment, wherein the oil-in-water emulsion has less than 0.85 ppm acetaldehyde.
B10. The process of any preceding embodiment, wherein the oil-in-water emulsion comprises squalene and the emulsion has less than 661 picograms of polychlorinated biphenyls (PCBs) per gram of squalene (toxic equivalent TEQ).
B11. A method for preparing (i) a vaccine composition, comprising preparing an oil-in-water emulsion according to any one of embodiments B1 to B10 and combining the emulsion with an antigen, or (ii) a vaccine kit comprising preparing an oil-in-water emulsion according to any one of claims 1 to 10 and packaging the emulsion into a kit as a kit component together with an antigen component.
B12. The method of embodiment B11, wherein the antigen is an influenza virus antigen; for example, wherein the combination of the emulsion and the antigen forms a vaccine composition and wherein the vaccine composition includes about 15 µg, about 10 µg, about 7.5 µg, about 5 µg, about 3.8 µg, about 1.9 µg, about 1.5 µg of hemagglutinin per influenza virus strain.

This invention is further illustrated by the following examples.

Examples

MF59 emulsion adjuvant with squalene, polysorbate 80, sorbitan trioleate and citrate buffer was prepared using the methods disclosed in References 10 to 12, with: preparation of a squalene/sorbitan triolate mixture and a solution of polysorbate 80 in citrate buffer; formation of a first emulsion by homogenization of these components using "type I" then "type II" circulation; formation of a second emulsion by microfluidisation (again using "type II" circulation) with an IXC-APM Z-channel arrangement, to reduce oil droplet diameter relative to the first emulsion; and filtration of the microfluidised emulsion through a hydrophilic double-layer PES membrane. For the "type II" circulation the emulsion was passed between two containers, but after the final homogenization or microfluidisation it was collected into a third (fresh) container. Batch sizes were 50 or 250 liters.

Two different types of non-aqueous polysorbate 80 were used. With reference to table 1 below, batch numbers 2111-2118 used polysorbate 80 which was not filtered prior to being used, whereas batch numbers 2119 onwards used polysorbate 80 which was prefiltered through a 20 µm polypropylene fleece filter capsule (SARTOPURE™ PP 2 MIDICAP™, 20 µm) at room temperature with a peristaltic pump, before being mixed with citrate buffer. When using a fresh SARTOPURE™ PP 2 MIDICAP™ 20 µm filter, the first 200 ml were discarded.

Table 1 shows the effect of this pre-filtration on the amount (ppm) of acetone, acetaldehyde and formaldehyde in the batches of final MF59 emulsion adjuvant which were produced. The thick line in table 1, under row 2118, indicates the batch at which prefiltration of the anhydrous polysorbate 80 was commenced. All of the batches below this line were manufactured using a method in which the anhydrous polysorbate 80 was prefiltered. Acetaldehyde levels above the line are all above 0.85 ppm, whereas levels below the line are all less than 0.70 ppm.

FIG. 1 shows a graphical depiction of the data in table 1 (including further batches). This FIGURE shows in clear visual terms that batches prior to batch number 2119 (i.e., those without a prefiltration step) have a higher acetaldehyde content than those produced after batch number 2119, (i.e., those for which the prefiltration step was included). Although the results show batch-to-batch variability, the inventor believes that the prefiltration contributes to the reduced carbonyl levels, and that the process is more robust by using prefiltered material.

TABLE 1

| Charge 549 . . . 010 | Squalene [36; 42] | Sorbitan Trioleate [4.1; 6.3] | Polysorbate 80 [4.1; 6.3] | Average Particle Size [135, 175] | Number of Large Particles $1 \times 10^7$ | Acetone ≤1.5 | Acetaldehyde ≤2.6 | Formaldehyde ≤0.2 |
|---|---|---|---|---|---|---|---|---|
| 2111 | 40.1 | 4.4 | 4.4 | 164 | 594890 | 0.22 | 0.89 | 0.03 |
| 2112 | 39.7 | 4.5 | 4.5 | 175 | 464840 | 0.22 | 0.87 | 0.03 |
| 2113 | 39 | 4.4 | 4.4 | 171 | 444140 | 0.18 | 0.86 | 0.03 |
| 2114 | 38.5 | 4.3 | 4.3 | 162 | 358150 | 0.22 | 0.86 | 0.03 |
| 2115 | 39 | 4.6 | 4.5 | 160 | 537910 | 0.24 | 0.86 | 0.03 |
| 2116 | 39.1 | 4.4 | 4.4 | 166 | 314300 | 0.21 | 0.85 | 0.03 |
| 2117 | 38.7 | 4.7 | 4.5 | 161 | 600830 | 0.28 | 0.86 | 0.03 |
| 2118 | 39.8 | 4.7 | 4.5 | 166 | 880760 | 0.12 | 0.85 | 0.03 |
| 2119 | 39.3 | 4.6 | 4.4 | 166 | 695530 | 0.06 | 0.67 | 0.03 |
| 2120 | 39.5 | 4.6 | 4.5 | 170 | 482050 | 0.06 | 0.39 | 0.04 |
| 2121 | 39.9 | 4.1 | 4.2 | 161 | 792860 | 0.06 | 0.4 | 0.04 |
| 2122 | 38.9 | 4.3 | 4.2 | 172 | 500990 | 0.08 | 0.39 | 0.04 |
| 2123 | 39.4 | 4.8 | 4.7 | 162 | 509460 | 0.06 | 0.4 | 0.04 |
| 2124 | 39.3 | 4.6 | 4.6 | 163 | 518690 | 0.29 | 0.45 | 0.05 |
| 2125 | 38.6 | 4.6 | 4.6 | 168 | 1092500 | 0.36 | 0.44 | 0.05 |
| 2126 | 38.3 | 4.5 | 4.4 | 167 | 409460 | 0.22 | 0.43 | 0.05 |
| 2127 | 37.6 | 4.4 | 4.4 | 169 | 1196670 | 0.21 | 0.43 | 0.05 |
| 2128 | 38.3 | 4.5 | 4.4 | 167 | 334780 | 0.18 | 0.44 | 0.05 |
| 2129 | 38.2 | 4.6 | 4.4 | 168 | 534930 | 0.2 | 0.43 | 0.06 |
| 2130 | 38.1 | 4.4 | 4.5 | 168 | 434100 | 0.12 | 0.42 | 0.05 |
| 2131 | 38.3 | 4.4 | 4.4 | 174 | 321950 | 0.11 | 0.42 | 0.05 |
| 2132 | 39.7 | 4.6 | 4.5 | 172 | 418630 | 0.11 | 0.43 | 0.05 |
| 2133 | 39.6 | 4.5 | 4.5 | 175 | 524520 | 0.06 | 0.45 | 0.05 |
| 2134 | 39.6 | 4.5 | 4.5 | 165 | 431690 | 0.06 | 0.47 | 0.06 |
| 2135 | 39.5 | 4.5 | 4.6 | 164 | 428420 | 0.07 | 0.49 | 0.06 |

REFERENCES

[1] WO90/14837.
[2] Podda & Del Giudice (2003) Expert Rev Vaccines 2:197-203.
[3] Podda (2001) Vaccine 19: 2673-2680.

[4] Vaccine Design: The Subunit and Adjuvant Approach (eds. Powell & Newman) Plenum Press 1995 (ISBN 0-306-44867-X).
[5] Vaccine Adjuvants: Preparation Methods and Research Protocols (Volume 42 of Methods in Molecular Medicine series). ISBN: 1-59259-083-7. Ed. O'Hagan.
[6] New Generation Vaccines (eds. Levine et al.). 3rd edition, 2004. ISBN 0-8247-4071-8.
[7] Kishore et al, (2011) Pharm Res 25:1194-1210.
[8] Maggio (2012), J. Excipients and Food Chem 3(2): 45-53.
[9] Yeo et al, (1992) Lipids 27(1):50-53.
[10] WO2011/067669
[11] WO2011/067673
[12] WO2011/067672
[13] Light Scattering from Polymer Solutions and Nanoparticle Dispersions (W. Schartl), 2007. ISBN: 978-3-540-71950-2.
[14] O'Hagan (2007) Expert Rev Vaccines 6(5):699-710.
[15] EP B 2029170
[16] Garçon et al. (2012) Expert Rev Vaccines 11:349-66.
[17] WO2008/043774.
[18] WO2010/023551
[19] Brito et al. (2011) Vaccine 29:6262-6268.
[20] WO94/26683.
[21] He et al. (2002) J Agric Food Chem 50:368-72.
[22] WO2011/141819
[23] U.S. Pat. No. 8,092,813.
[24] WO2007/052155.
[25] Hoffmann et al. (2002) Vaccine 20:3165-3170.
[26] Subbarao et al. (2003) Virology 305:192-200.
[27] Liu et al. (2003) Virology 314:580-590.
[28] Ozaki et al. (2004) J. Virol. 78:1851-1857.
[29] Webby et al. (2004) Lancet 363:1099-1103.
[30] WO97/37000.
[31] Brands et al. (1999) Dev Biol Stand 98:93-100.
[32] Halperin et al. (2002) Vaccine 20:1240-7.
[33] Tree et al. (2001) Vaccine 19:3444-50.
[34] Kistner et al. (1998) Vaccine 16:960-8.
[35] Kistner et al. (1999) Dev Biol Stand 98:101-110.
[36] Bruhl et al. (2000) Vaccine 19:1149-58.
[37] Pau et al. (2001) Vaccine 19:2716-21.
[38] WO01/22992.
[39] Hehme et al. (2004) Virus Res. 103(1-2):163-71.
[40] Treanor et al. (1996) J Infect Dis 173:1467-70.
[41] Keitel et al. (1996) Clin Diagn Lab Immunol 3:507-10.
[42] Williamson et al. (2006) Infection and Immunity 74: 961-7.
[43] Loukas et al. (2005) PLoS Med 2(10): e295.
[44] EPA 0139417.
[45] Harper et al. (2004) Lancet 364(9447):1757-65.
[46] J Toxicol Clin Toxicol (2001) 39:85-100.
[47] Demicheli et al. (1998) Vaccine 16:880-884.
[48] Stepanov et al. (1996) J Biotechnol 44:155-160.
[49] Banzhoff (2000) Immunology Letters 71:91-96.
[50] WO02/097072.
[51] Greenbaum et al. (2004) Vaccine 22:2566-77.
[52] Zurbriggen et al. (2003) Expert Rev Vaccines 2:295-304.
[53] Piascik (2003) J Am Pharm Assoc (Wash D.C.). 43:728-30.
[54] Mann et al. (2004) Vaccine 22:2425-9.
[55] Halperin et al. (1979) Am J Public Health 69:1247-50.
[56] Herbert et al. (1979) J Infect Dis 140:234-8.
[57] Chen et al. (2003) Vaccine 21:2830-6.

The various features and embodiments of the present invention, referred to in individual sections above apply, as appropriate, to other sections, mutatis mutandis. Consequently, features specified in one section may be combined with features specified in other sections, as appropriate.

Those skilled in the art will recognize, or be able to ascertain using no more than routine experimentation, many equivalents to the specific embodiments of the invention described herein. Such equivalents are intended to be encompassed by the following claims.

The invention claimed is:

1. A process for preparing an oil-in-water emulsion comprising steps of:
    (a) purifying polysorbate 80 by filtering polysorbate 80 through a filter having a pore size between 5-50 μm; and
    (b) forming the oil-in-water emulsion by either:
        i) combining the purified polysorbate 80 with an aqueous component and adding an oil component; or
        ii) combining the purified polysorbate 80 with an oil component and adding an aqueous component.

2. The process of claim 1, wherein the filter is a polypropylene filter.

3. The process of claim 1, wherein the oil-in-water emulsion formed in step (b) is homogenized.

4. The process of claim 1, wherein the oil-in-water emulsion formed in step (b) is microfluidized.

5. The process of claim 3, wherein step (b) further comprises sterile filtration of the homogenized oil-in-water emulsion.

6. The process of claim 1, wherein the oil-in-water emulsion is a vaccine adjuvant including squalene.

7. The process of claim 6, wherein the oil-in-water emulsion comprises squalene, the polysorbate 80, and sorbitan trioleate.

8. The process of claim 1, wherein the oil-in-water emulsion has less than 0.85 ppm acetaldehyde.

9. The process of claim 1, wherein the oil-in-water emulsion comprises squalene and the emulsion has less than 661 picograms of polychlorinated biphenyls per gram of squalene (toxic equivalent TEQ).

10. A method for preparing (i) a vaccine composition, comprising preparing an oil-in-water emulsion according claim 1 and combining the emulsion with an antigen, or (ii) a vaccine kit comprising preparing an oil-in-water emulsion according to claim 1 and packaging the emulsion into a kit as a kit component together with an antigen component.

11. The method of claim 10, wherein the antigen is an influenza virus antigen.

12. The process of claim 4, wherein step (b) comprises sterile filtration of the microfluidized emulsion.

13. The method of claim 11, wherein the combination of the emulsion and the antigen forms a vaccine composition and wherein the vaccine composition includes about 15 μg, about 10 μg, about 7.5 μg, about 5 μg, about 3.8 μg, about 1.9 μg, or about 1.5 μg of hemagglutinin per influenza virus strain.

14. A process for preparing an oil-in-water emulsion comprising steps of:
    (a) purifying a composition comprising polysorbate 80 and an aqueous component by filtering the composition through a filter having a pore size between 5-50 μm; and
    (b) forming the oil-in-water emulsion by combining the purified composition comprising polysorbate 80 and the aqueous component with an oil component.

* * * * *